United States Patent
Yokosawa et al.

(10) Patent No.: US 11,428,769 B2
(45) Date of Patent: Aug. 30, 2022

(54) MAGNETIC RESONANCE IMAGING DEVICE, CALCULATION DEVICE FOR GENERATION OF IMAGING PARAMETER SET, AND IMAGING PARAMETER SET GENERATION PROGRAM

(71) Applicant: HITACHI, LTD., Tokyo (JP)

(72) Inventors: Suguru Yokosawa, Tokyo (JP); Yo Taniguchi, Tokyo (JP); Tomoki Amemiya, Tokyo (JP); Toru Shirai, Tokyo (JP); Hisaaki Ochi, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 358 days.

(21) Appl. No.: 16/756,177

(22) PCT Filed: Aug. 24, 2018

(86) PCT No.: PCT/JP2018/031429
§ 371 (c)(1),
(2) Date: Apr. 15, 2020

(87) PCT Pub. No.: WO2019/087543
PCT Pub. Date: May 9, 2019

(65) Prior Publication Data
US 2020/0278411 A1    Sep. 3, 2020

(30) Foreign Application Priority Data
Nov. 6, 2017    (JP) ............... JP2017-213762

(51) Int. Cl.
*G01R 33/561*    (2006.01)
*G01R 33/50*    (2006.01)
(Continued)

(52) U.S. Cl.
CPC .......... *G01R 33/5613* (2013.01); *A61B 5/055* (2013.01); *G01R 33/50* (2013.01); *G01R 33/5602* (2013.01); *G01R 33/5616* (2013.01)

(58) Field of Classification Search
CPC ................ G01R 33/5613; G01R 33/50; G01R 33/5602; G01R 33/5616; G01R 33/543; G01R 33/546; A61B 5/055
(Continued)

(56) References Cited

U.S. PATENT DOCUMENTS

| | | | |
|---|---|---|---|
| 8,314,618 B2 | 11/2012 | Bieri et al. | |
| 8,798,718 B2 * | 8/2014 | Schmitt ................. | A61B 5/055 324/309 |

(Continued)

FOREIGN PATENT DOCUMENTS

| | | |
|---|---|---|
| JP | 2011-024926 A | 2/2011 |
| WO | 2017/013801 A1 | 1/2017 |
| WO | 2017/022136 A1 | 2/2017 |

OTHER PUBLICATIONS

International Preliminary Report on Patentability received in corresponding International Application No. PCT/JP2018/031429 dated May 12, 2020.

(Continued)

*Primary Examiner* — Christopher P McAndrew
(74) *Attorney, Agent, or Firm* — Mattingly & Malur, PC (57) ABSTRACT

An MRI device for executing an imaging operation at least three times or more with a different combination of at least a repetition time and a flip angle in the same imaging sequence, includes: a receiving unit which receives information specifying an imaging target and a constraint condition relating to an imaging time or quantitative value accuracy; and a scan parameter set generation unit which calculates at least three or more scan parameter sets having a different combination of at least the repetition time and the (Continued)

flip angle on the basis of the constraint condition. The MRI device uses three or more scan parameter sets generated by the optimal scan parameter set generation unit and calculates quantitative values (T1, T2, and the like) of the imaging target from a plurality of images obtained by the imaging operation.

13 Claims, 9 Drawing Sheets

(51) Int. Cl.
    *G01R 33/56*     (2006.01)
    *A61B 5/055*     (2006.01)

(58) Field of Classification Search
    USPC .......................................................... 600/410
    See application file for complete search history.

(56) References Cited

U.S. PATENT DOCUMENTS

| | | | |
|---|---|---|---|
| 10,288,710 B2* | 5/2019 | Bielmeier | G01R 33/36 |
| 2006/0017437 A1* | 1/2006 | Vu | G01R 33/583 |
| | | | 324/309 |
| 2010/0128952 A1* | 5/2010 | Schmitt | A61B 6/03 |
| | | | 382/131 |
| 2015/0204953 A1* | 7/2015 | Ookawa | G01R 33/4833 |
| | | | 324/309 |
| 2015/0285885 A1* | 10/2015 | Feiweier | G01R 33/36 |
| | | | 324/309 |
| 2017/0131373 A1* | 5/2017 | Takeshima | G01R 33/50 |
| 2017/0209067 A1 | 7/2017 | Taniguchi et al. | |

OTHER PUBLICATIONS

International Search Report of PCT/JP2018/031429 dated Nov. 27, 2018.

* cited by examiner

MAGNETIC RESONANCE IMAGING DEVICE, CALCULATION DEVICE FOR GENERATION OF IMAGING PARAMETER SET, AND IMAGING PARAMETER SET GENERATION PROGRAM

TECHNICAL FIELD

The present invention relates to setting of scan parameters in quantitative value calculation by a magnetic resonance imaging device.

BACKGROUND ART

A magnetic resonance imaging (MRI) device is a medical image diagnostic device that mainly uses a nuclear magnetic resonance phenomenon of protons. Signals obtained by the MRI device are determined by a quantitative value (for example, T1: longitudinal relaxation time, T2: lateral relaxation time or T2*: apparent lateral relaxation time, PD: proton density, D: diffusion coefficient, or the like) or an imaging condition of an inspection target. In the MR inspection, a user selects a pulse sequence as an imaging condition and a parameter for determining the condition (referred to as a scan parameter) so as to obtain an emphasized image in which a relative difference between quantitative values of living tissue is emphasized. When changing the degree of emphasis or the quantitative value of the target tissue, it is necessary to select another pulse sequence or change the scan parameters. Generally, the MR image has a trade-off relationship of a signal-to-noise ratio, an imaging time, and a resolution. The scan parameters relating to these are adjusted while checking the balance between the item that the user wants to prioritize and the acceptable quality.

The MR signal depends on the hardware of the device in addition to the above-described scan parameters. In this regard, a technique has been developed for generating a quantitative value image from an MR image by removing the influence of hardware-dependent parameters (device parameters). The quantitative value image is an image in which a quantitative value of a living tissue is a pixel value. In recent years, a clinical usefulness of the image in early diagnosis of knee osteoarthritis and diagnosis of a necrotic site of myocardium has been reported. Since the quantitative value image does not need to consider device parameters, this image facilitates standardization of MR images, which had been difficult when conducting clinical research across multiple centers.

As a method of calculating a quantitative value image, for example, there has been proposed a method of acquiring an image at two or more different RF phase increment values in a Steady State of Free Precession (SSFP) sequence to which RF spoiling is added and calculating T2 (Patent Document 1). Further, a method of acquiring a plurality of images while changing scan parameters using an RF spoiled GRASS sequence and estimating a quantitative value at the same time using a luminance function obtained by numerical simulation has been proposed (Patent Document 2).

CITATION LIST

Patent Document

Patent Document 1: U.S. Pat. No. 8,314,618
Patent Document 2: JP-A-2011-24926

SUMMARY OF THE INVENTION

Technical Problem

In the methods described in Patent Document 1 and Patent Document 2, the quantitative value is estimated by performing a fitting process on pixel values of a plurality of images captured while changing the scan parameters to the luminance function (relational expression between the scan parameter and the quantitative value) obtained by a theoretical formula or a simulation. In this way, in the method of estimating the quantitative value by the fitting process, the accuracy of the quantitative value calculation largely depends on the scan parameters. In the method described in Patent Document 1, for the phase increment value of the RF pulse, the range of the value to be set is mentioned as the scan parameter to be changed, but the scan parameter other than the phase increment value is fixed. Accordingly, these contributions to the calculation accuracy of the quantitative value T2 are not considered.

Meanwhile, in the method described in Patent Document 2, the scan parameters to be changed are a repetition time (TR) and a flip angle (FA), and an example of a scan parameter set is proposed. Here, when a user wishes to adjust the imaging time by changing TR, it is necessary to generate the scan parameter set again. At this time, since the accuracy is not sufficiently guaranteed by the scan parameter set in which only TR is simply adjusted to be short, it is required to extract an optimal one among candidates of a plurality of scan parameter sets in which a combination of TR and a flip angle is changed. Thus, in this method, a problem arises in that the user cannot easily adjust the scan parameter.

Therefore, an object of the invention is to provide an optimal scan parameter set while securing a degree of freedom in setting of scan parameters by a user in MR imaging (referred to quantitative value imaging) that generates a quantitative value image.

Solution to Problem

In the invention, a plurality of scan parameter sets used in MR imaging (hereinafter, referred to as quantitative value imaging) that generates a quantitative value image are determined by using an index relating to an imaging time and information specifying an imaging target received during an imaging operation. The index relating to the imaging time includes factors that influence the imaging time, such as the TR of each imaging, the average value and total value of TR, and the number of times of imaging (the number of scan parameter sets) in addition to the imaging time.

An aspect of the invention relates to an MRI device including: a target receiving unit which receives information specifying an imaging target from a user; a measurement unit which acquires a plurality of images of the imaging target by executing measurement a plurality of times; a quantitative value calculation unit which calculates a quantitative value of the imaging target by using the plurality of images acquired by the measurement unit; and a scan parameter set generation unit which generates a scan parameter set used for the plurality of measurements, wherein the scan parameter set generation unit estimates an error of the quantitative value when a value of a scan parameter is changed by using information specifying the imaging target received by the target receiving unit and determines a combination of the scan parameters by using an index relating to an imaging time and an error estimation value.

The information specifying the imaging target includes, for example, information on a tissue included in the imaging target or a typical value (standard value) of a quantitative value of the tissue.

Another aspect of the invention relates to a computer, that is, a scan parameter generation device having a function of the scan parameter set generation unit described above and still another aspect relates to a program which executes a function of a scan parameter set generation unit by the computer. Specifically, the program is a program causing the computer to execute steps of: receiving information specifying an imaging target; selecting a standard value of a quantitative value of the imaging target received in the receiving step from standard values of one type or more of quantitative values obtained in advance for a plurality of imaging targets; calculating an error estimation value of the quantitative value obtained from an image captured by using the scan parameter set for each of the plurality of scan parameter sets using the selected standard value of the quantitative value; and determining an optimal scan parameter by using an index relating to an imaging time and the error estimation value of the quantitative value as constraints.

Advantageous Effects of the Invention

According to the invention, since an optimal parameter set is provided in response to a condition specified by the user, the setting of the scan parameter during the quantitative value measurement is facilitated and the user's convenience is improved.

MODE FOR CARRYING OUT THE INVENTION

Hereinafter, an embodiment of an MRI device according to the invention will be described.

First Embodiment

Figure 1:
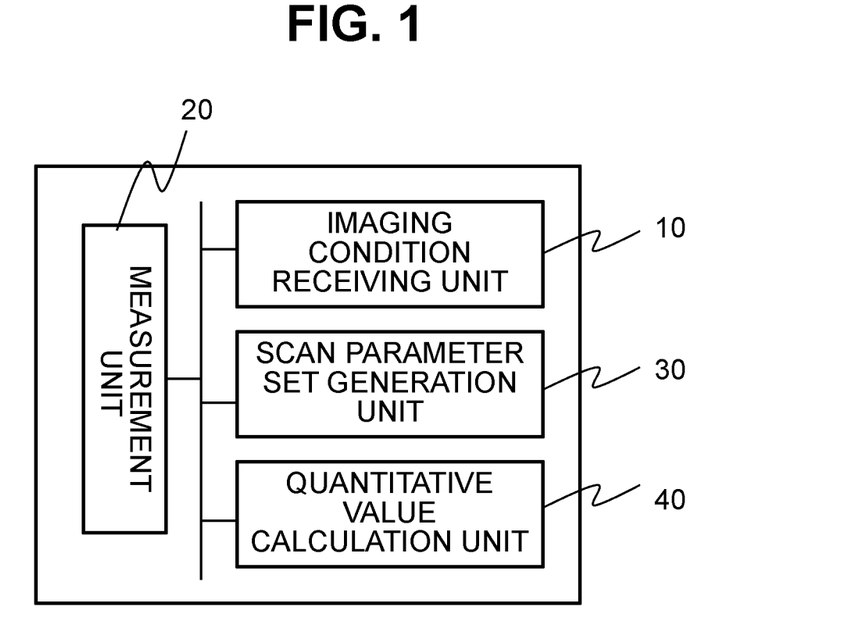
FIG. 1 is a functional block diagram of an MRI device of a first embodiment.

An MRI device of this embodiment includes, as illustrated in FIG. 1, an imaging condition receiving unit 10, a measurement unit 20, a quantitative value calculation unit 40, and a scan parameter set generation unit 30.

The imaging condition receiving unit 10 receives information that specifies an imaging condition or an imaging target from a user. The measurement unit captures N images of the same imaging target by executing an imaging sequence using at least a repetition time TR and a flip angle FA as a scan parameter N times (N is 3 or more) by changing a combination of the values of the repetition time TR and the flip angle FA. The quantitative value calculation unit calculates one type or more of quantitative values on the basis of N images captured by the measurement unit. A scan parameter set generation unit generates N types of combinations of the values of the repetition time TR and the flip angle FA and sets the combination as the repetition time TR and the flip angle FA when the measurement unit executes the imaging sequence N times. At that time, the scan parameter set generation unit selects a standard value of the quantitative value of the imaging target received by the imaging condition receiving unit from standard values of one type or more of the quantitative values obtained in advance for the plurality of imaging targets and generates N types of combinations of the values of the repetition time TR and the flip angle FA when the imaging time of the imaging sequence is equal to or smaller than a predetermined value or the error of the physical property value calculated by the quantitative value calculation unit is equal to or smaller than a predetermined value by using the standard value of the quantitative value.

The measurement unit executes measurement N times by the same imaging sequence using N types of scan parameter sets generated by the scan parameter set generation unit and acquires N images.

According to the MRI device of this embodiment, an optimal scan parameter set is determined depending on whether priority is given to the shortening of the imaging time or the accuracy of calculating the quantitative value. Accordingly, the degree of freedom in setting imaging conditions by the user is increased and the accuracy of the calculated quantitative value can be increased. The priority to the shortening of the imaging time or the accuracy of calculating the quantitative value may be received by the input of the user or may be determined by the scan parameter set calculation unit from the imaging conditions set by the user.

Hereinafter, a more detailed embodiment will be described based on this embodiment.

Second Embodiment

Figure 2:
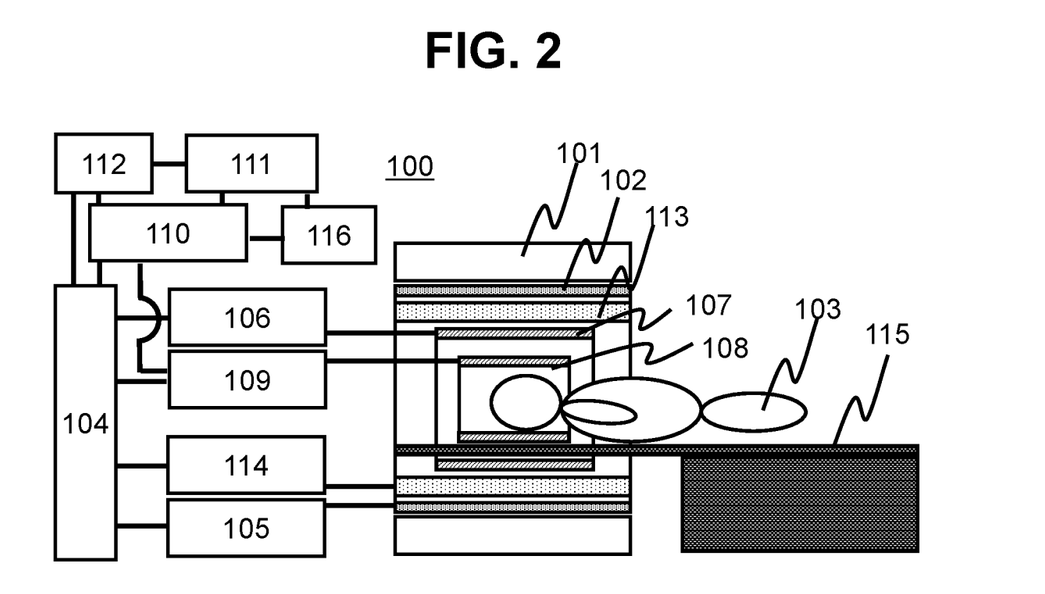
FIG. 2 is a block diagram illustrating a typical configuration of an MRI device of a second embodiment.

First, a typical configuration of the MRI device will be described. FIG. 2 is a block diagram illustrating an embodiment of the MRI device. As illustrated in FIG. 2, an MRI device 100 of this embodiment includes a magnet 101 which generates a static magnetic field, a gradient magnetic field coil 102 which generates a gradient magnetic field, an RF coil 107 which irradiates a subject 103 with a high-frequency magnetic field pulse (hereinafter, an RF pulse), an RF probe 108 which detects an echo signal generated from the subject 103, and a bed (table) 115 which places the subject (for example, a living body) 103 in a static magnetic field space generated by the magnet 101.

The gradient magnetic field coil 102 includes three sets of gradient magnetic field coils that generate a gradient magnetic field in three axial directions orthogonal to each other and can give position information in an arbitrary direction by appropriately combining these.

Further, the MRI device 100 of this embodiment includes a gradient magnetic field power supply 105 which drives each coil constituting the gradient magnetic field coil 102, a high-frequency magnetic field generator 106 which drives the RF coil 107, a receiver 109 which receives an echo signal detected by the RF probe 108, a sequencer 104 which sends a command to the gradient magnetic field power supply 105 and the high-frequency magnetic field generator 106, generates a gradient magnetic field and a high-frequency magnetic field, and sets a nuclear magnetic resonance frequency to be detected to the receiver 109, a computer 110 which applies signal processing to the detected signal, a display device 111 which displays a result of processing on the computer 110, a storage device 112 which stores a process result, and an input device 116 which receives an instruction from the user. When the display device 111 and the input device 116 are disposed adjacent to each other, the display device 111 displays a user interface (UI) so that the user and the device are operated in an interactive manner. Further, the storage device 112 stores various data required for the process in the computer 110.

Further, the MRI device 100 may further include a SIMM coil 113 and a SIMM power supply 114 driving the SIMM coil 113 when there is a need to adjust static magnetic field uniformity. The SIMM coil 113 has a plurality of channels and generates an additional magnetic field for correcting the static magnetic field by the current supplied from the SIMM power supply 114. The current flowing through each of the channels constituting the SIMM coil 113 when adjusting the static magnetic field uniformly is controlled by the sequencer 104.

The functions of the measurement unit 20 (FIG. 1) of the MRI device 100 are realized by the above-described units. That is, an RF pulse is applied to the subject 103 via the RF coil 107 and a gradient magnetic field pulse for giving position information such as slice selection and phase encoding to an echo signal is applied by the gradient magnetic field coil 102 under the control of the sequencer 104. Further, a signal generated from the subject 103 is received by the RF probe 108 and a detected signal is sent to the computer 110 so that signal processing such as image reconstruction is executed. Additionally, the storage device 112 may store not only the result of the signal processing but also the detected signal itself, imaging conditions, and the like if necessary.

The computer 110 functions as a calculation unit which includes a CPU and a memory and processes received signals and a control unit which controls the entire operation of the MRI device 100. In this embodiment, as the calculation unit, the processing of the quantitative value calculation unit 40 and the scan parameter set generation unit 30 illustrated in FIG. 1 is executed in addition to the above-described image reconstruction. However, the functions of the quantitative value calculation unit 40 and the scan parameter set generation unit 30 may be realized by a computer different from the MRI device that executes imaging.

For example, the control unit sends an instruction to the sequencer 104 so that each unit operates at the timing and intensity programmed in advance, controls the operation of each unit included in the MRI device 100, and executes measurement. Among the above-described programs, the pulse sequence is that particularly describes timing or intensity of a high-frequency magnetic field, a gradient magnetic field, and a signal reception. There are various pulse sequences depending on the imaging method and these basic pulse sequences are stored in the storage device 112 in advance.

In actual imaging, the basic pulse sequence is adjusted according to the imaging part or imaging purpose. This adjustment parameter is called a scan parameter and is input by the user via the input device 116. The scan parameter includes a repetition time (TR), an echo time (TE), a flip angle (FA) for determining RF pulse intensity, a frequency encoding number, a phase encoding number, a slice thickness, the number of slices, a slice interval, a reception bandwidth, and the like. The measurement is executed according to the pulse sequence and the scan parameter required for controlling the pulse sequence. In the quantitative value imaging, measurement is executed by changing each value of a plurality of scan parameters among the above-described scan parameters. Here, a combination of scan parameters each of which value is changed is referred to as a scan parameter set.

Figure 3:
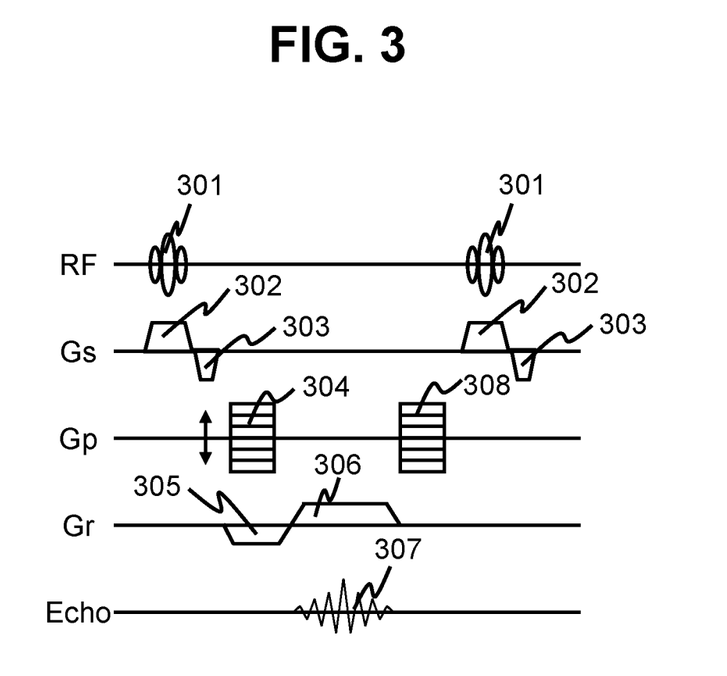
FIG. 3 is a time chart of a pulse sequence which can be executed in the second embodiment.

As an example of the pulse sequence used for capturing a quantitative value image, an RF-spoiled GRASS sequence is shown in FIG. 3. In this drawing, RF, Gs, Gp, Gr, and Echo respectively represent a high-frequency magnetic field, a slice gradient magnetic field, a phase encoding gradient magnetic field, a readout gradient magnetic field, and an echo signal. An RF pulse 302 is irradiated together with the application of a slice gradient magnetic field pulse 301 to excite the magnetization of a certain slice in a target object. Next, an echo signal 307 is measured while applying a readout gradient magnetic field pulse 306 for adding position information in the readout direction after applying a slice rephase gradient magnetic field pulse 303, a phase encoding gradient magnetic field pulse 304 for adding position information in the phase encoding direction to the magnetization phase, and a readout gradient magnetic field 305 for dephase. Finally, a phase encoding gradient magnetic field pulse 308 for dephase is applied. The above-described sequence is repeated with the repetition time TR while changing the intensity (phase encoding amount kp) of the phase encoding gradient magnetic field pulses 304 and 308 and changing the phase of the RF pulse by an increment value θ (for example, 117°) (the phase of the n-th RF pulse is $\phi(n)=\phi(n-1)+117n$) and an echo required for obtaining one image is measured. Each echo is disposed in a k-space and an image is reconstructed by two-dimensional inverse Fourier transform. This pulse sequence has a feature that an image in which T1 (longitudinal relaxation time) is emphasized can be obtained.

In the quantitative value imaging, the same pulse sequence (RF-spoiled GRASS sequence) is executed by using a plurality of different scan parameter sets. In the MRI device of this embodiment, one having different combinations of at least values of the repetition time and the flip angle is used as the scan parameter set. The computer 110 (the scan parameter set generation unit 30) calculates a combination of an optimal scan parameter set on the basis of information for an imaging condition or an inspection object set by the user via the input device 116. The sequencer 104 controls each unit of the MRI device so as to execute a plurality of measurements by the above-described pulse sequence using the combination of the scan parameter sets calculated by the computer 110.

Figure 4:
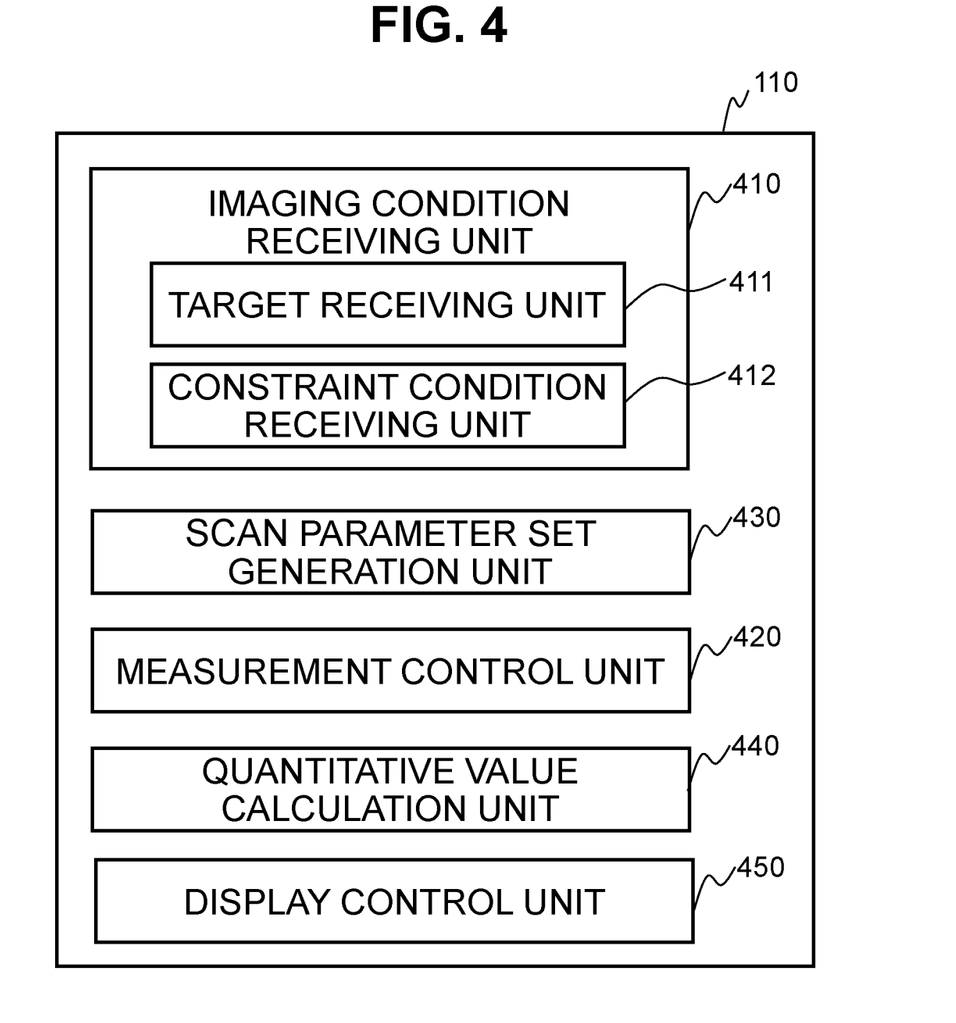
FIG. 4 is a functional block diagram of a computer of the second embodiment.

FIG. 4 illustrates the configuration of the computer 110 of this embodiment functioning as the calculation unit and the control unit. The computer 110 includes, as illustrated in FIG. 4, an imaging condition receiving unit 410 which receives an imaging condition, a scan parameter set generation unit 430 which generates at least three or more scan parameter sets having a different combination of at least the repetition time and the flip angle, a measurement control unit 420 which executes the same pulse sequence on the basis of the generated scan parameter set, a quantitative value calculation unit 440 which calculates a quantitative value by using a plurality of images having different pixel values, and a display control unit 450 which controls a GUI or an image displayed on the display device 111.

The imaging condition receiving unit 410 includes a target receiving unit 411 which receives a condition relating to an imaging target such as an imaging part or an imaging target organ and a constraint condition receiving unit 412 which receives either an index relating to the imaging time or an index relating to the estimation accuracy of the quantitative value. The index received by the constraint condition receiving unit 412 becomes the constraint condition when the scan parameter set generation unit 430 determines an optimal scan parameter set for a specified imaging target.

These functions of the computer 110 are mainly achieved by a program incorporated in the CPU. In addition, some or all of the quantitative value calculation may be realized by hardware such as an ASIC or an FPGA.

Figure 5:
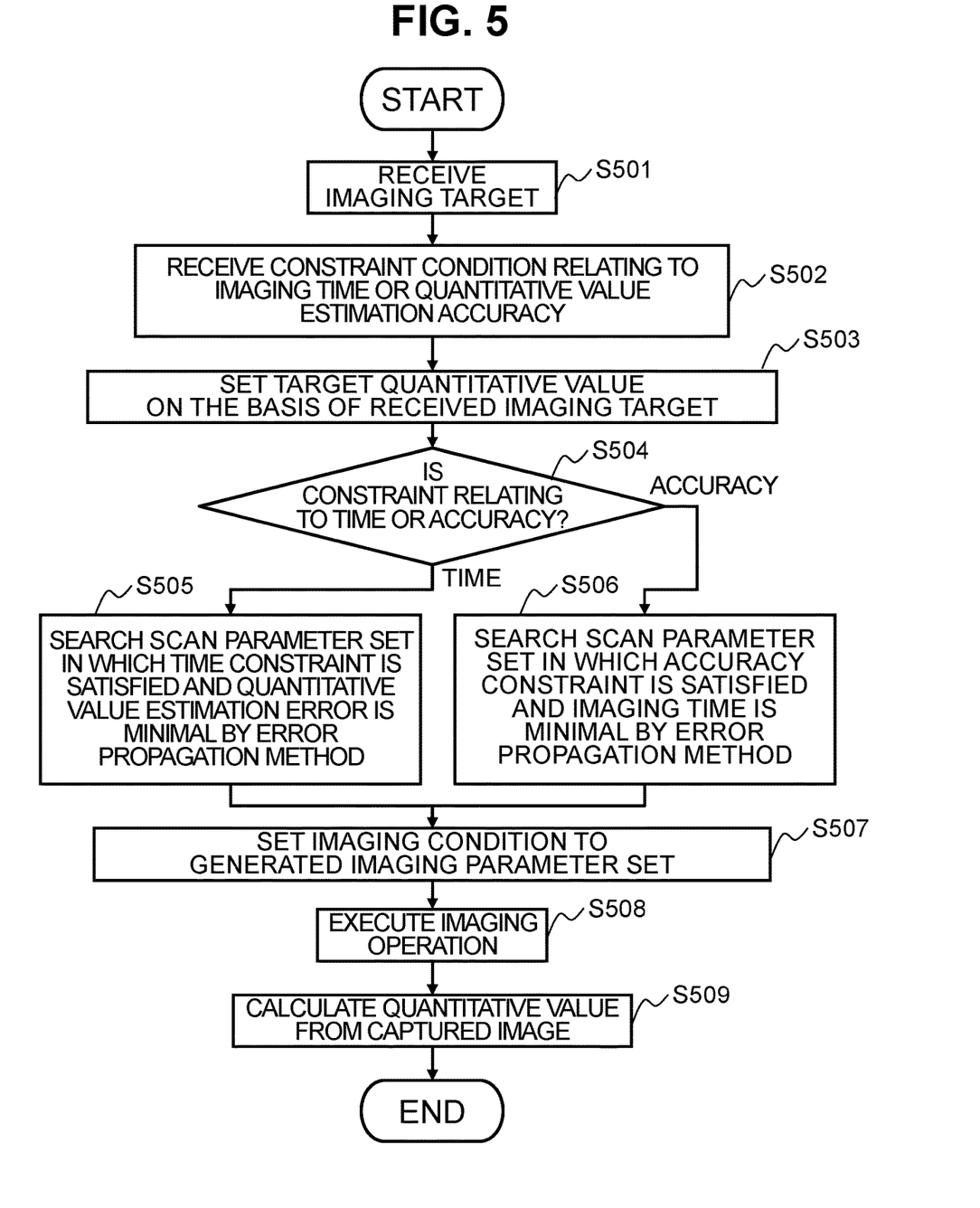
FIG. 5 is an example of a flow of the computer of the second embodiment.

Next, a flow of a process of the computer 110 of this embodiment will be described. FIG. 5 illustrates an outline of a flow of a process. First, the display control unit 450 displays an UI for setting an imaging condition on the display device 111 and receives an imaging target input from the user via the UI and the input device 116 by the target receiving unit 411 (step S501). Further, constraint conditions on the imaging time or the estimation accuracy of the quantitative value input from the user via the UI and the input device 116 are received by the constraint condition receiving unit 412 (step S502).

Next, in the scan parameter set generation unit 430, the quantitative value information of the imaging target is set on the basis of the imaging target received in step S501 (step S503). Further, in the scan parameter set generation unit 430, it is determined whether the constraint condition specified in step S502 is relating to the time or accuracy (step S504). In step S504, when it is determined that a time constraint is received, the scan parameter set generation unit 430 calculates at least three or more scan parameter sets in which the combination of at least the repetition time and the flip angle is different and the quantitative value estimation error is minimal while satisfying the specified time constraint according to the error propagation method (step S505). Alternatively, in step S504, when it is determined that an accuracy constraint is received, the scan parameter set generation unit 430 calculates at least three or more scan parameter sets in which the combination of at least the repetition time and the flip angle is different and the imaging time is minimal while satisfying the specified accuracy constraint according to the error propagation method (step S506).

Then, in the measurement control unit 420, the scan parameter set calculated in step S505 or step S506 is set as a measurement condition (step S507). In the measurement control unit 420, an imaging operation is executed at the set condition (step S508). Next, in the quantitative value calculation unit 440, a quantitative value is calculated from a plurality of images obtained by the imaging operation (step S509).

Hereinafter, details of the process of each unit will be described.

<Steps S501, S502>

Figure 6:
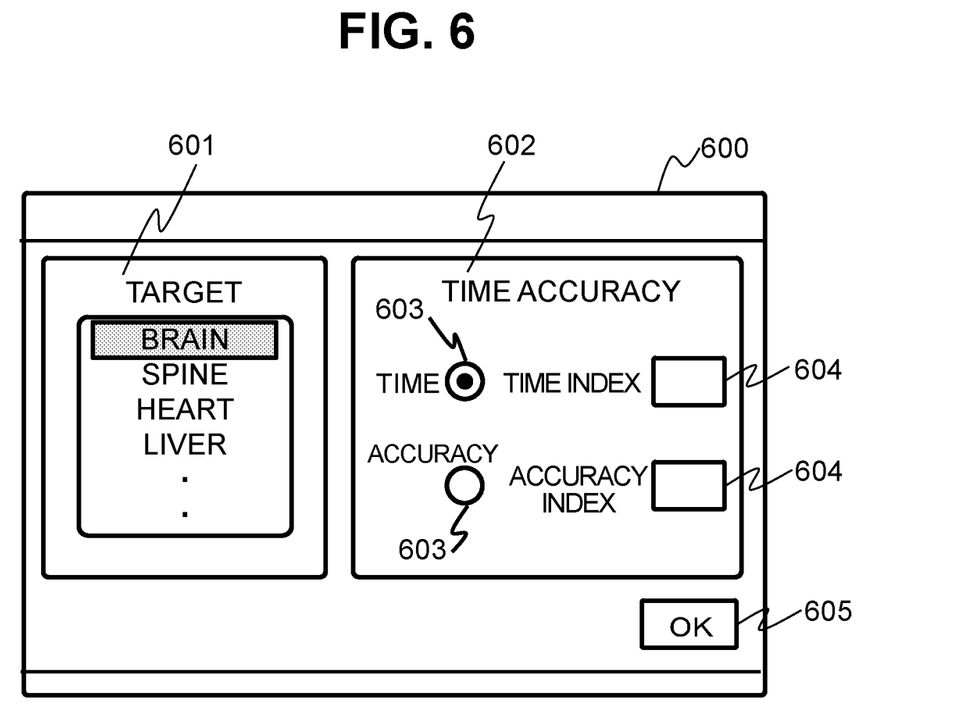
FIG. 6 is a diagram illustrating an example of a user interface of the second embodiment.

FIG. 6 illustrates an example of the UI for receiving the imaging condition displayed on the display device 111 by the display control unit 450. In an example illustrated in the drawing, a reception screen 600 includes a target receiving block 601 which receives a condition relating to an imaging target and a constraint condition receiving block 602. The target receiving block 601 is configured to select one item from imaging targets (brain, spine, heart, liver, and the like) listed in advance by the user. The constraint condition receiving block 602 includes a selection unit 603 which can select any one of time and accuracy by UI for receiving an index relating to the estimation accuracy of the quantitative value or the imaging time, and a numerical value input unit 604 which receives an numerical value input of an index relating to each of time and accuracy. As the index relating to time, for example, the total value of TR of the scan parameter set to be generated, the number of scan parameter sets (3 or more) and the like are input. As the accuracy index, for example, a threshold value for a relative error calculated by the error propagation method is input. Further, a confirmation button 605 for saving the input contents and proceeding to the next step S503 is provided.

<Step S503>

The scan parameter set generation unit 430 first sets the quantitative value information of the imaging target selected in step S501. The quantitative value information is a typical quantitative value (hereinafter, referred to as a reference value of a quantitative value) empirically obtained for each imaging target and is used for the calculation of the error propagation method in steps S505 and S506 described later. The quantitative value is, for example, proton density PD, sensitivity Sc of a reception coil, transmission sensitivity B1, longitudinal relaxation time T1, lateral relaxation time T2 or apparent lateral relaxation time T2*, or the like.

In this embodiment, the reference value of the quantitative value of the imaging target which can be selected by the user in the target receiving unit 411 is stored in the storage device 112 in advance as a table. The scan parameter set generation unit 430 calls the reference value of the selected imaging target by referring to the table of the quantitative value and the imaging target stored in the storage device 112 in response to the selection of the user in the target receiving unit 411. For example, when the subject is a brain, the called values are quantitative values of the main tissues of the brain, such as white matter, gray matter, cerebrospinal fluid, and fat.

<Steps S504, S505>

Figure 7:
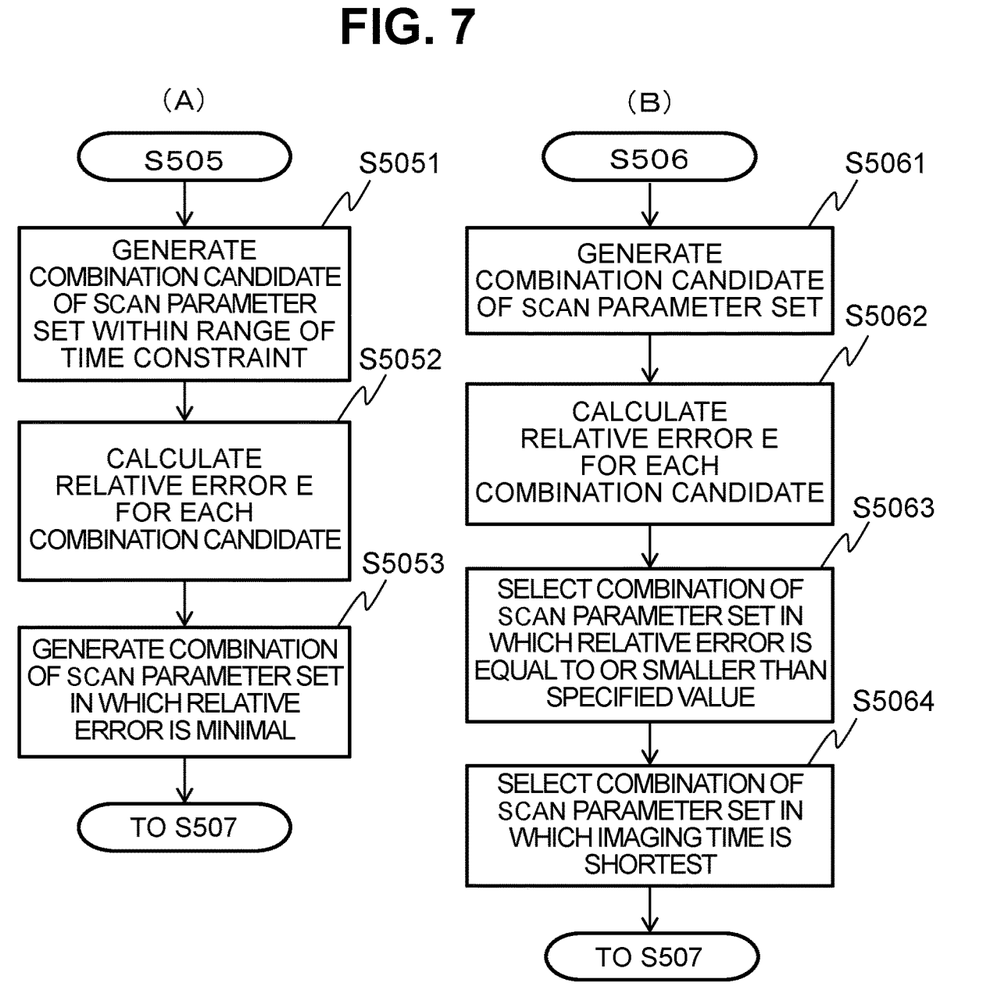
FIGS. 7(A) and 7(B) are diagrams respectively illustrating the detail of step S505 and step S506 of the flow of FIG. 5.

In step S504, when time priority is selected via the selection unit 603 (FIG. 6) and a time constraint condition is input via the time index 504, the constraint condition receiving unit 412 receives these conditions and the scan parameter set generation unit 430 generates a scan parameter set by an optimization method using the error propagation method under the received constraints. FIG. 7(A) illustrates details of step S505.

The scan parameter set targeted for the optimization method may be a brute force method, but in order to shorten the calculation time, it is preferable to narrow down the number of combinations of target scan parameter sets based on settable values of scan parameters (flip angle FA, repetition time TR, echo time TE, phase increment θ of RF pulse) (S5051). Specifically, for example, when candidates for settable values of the scan parameters are stored in the storage device 112 in advance and the number N of parameter sets is specified as a time index, the value of N is fixed and the scan parameter set in which the number of parameter sets is N is generated with a combination of candidates for each value. Alternatively, when the total value of TR of the scan parameter set is received as the time index, N may be set to 3 or more and only the combination in which the total value of TR matches the specified value may be selected from the scan parameter set generated by combining the scan parameter value candidates. Alternatively, both or one of TE and θ of the four scan parameters may be fixed and only the FA and TR may be generated from different combinations. This can prevent the number of combinations from increasing.

When the combination (combination candidate) of the target scan parameter set is determined, a perturbation of a quantitative value is calculated for each combination candidate from a luminance value of an image obtained when each scan parameter set is used and an error is estimated (S5052).

A luminance value I of an image acquired by a pulse sequence executed in this embodiment can be represented by a luminance function of a scan parameter and a quantitative value of an imaging target as in the following equation (1).

[Math. 1]
$$I=f(a, B1, T1, T2^*, FA, TR, TE, \theta) \quad (1)$$

Here, a is a proportional coefficient including the proton density, the sensitivity of the reception coil, and the reception gain, B1 is the transmission sensitivity, T1 is the longitudinal relaxation time, T2* is the apparent lateral relaxation time, FA is the flip angle, TR is the repetition time, TE is the echo time, and θ is the phase increment of RF (high-frequency magnetic field). a, B1, T1, and T2* are quantitative values and FA, TR, TE, and θ are scan parameters. The luminance function is known in a general pulse sequence and can be obtained as a numerical interpolation function by solving a Bloch's equation.

The perturbation ($\Delta a, \Delta B1, \Delta T1, \Delta T2^*$) of the quantitative value is expressed by the following equation (2) by deriving the function f of the equation (1) from a quadratic function approximation when the number of scan parameter sets is N and the i-th scan parameter set is xi=(FAi, TRi, TEi, θi), where i is an integer of 1 to N.

[Math. 2]
$$(\Delta a \quad \Delta B1 \quad \Delta T1 \quad \Delta T2^*) = \sum_{j=1}^{N} \left| \left( \sum_{i=1}^{N} \nabla^2 f(x_i) \right)^{-1} \nabla f(x_j) \right| \quad (2)$$

Here, $\nabla f$ is a gradient vector, and $\nabla^2 f$ is a Hessian matrix, which are respectively represented by equations (3) and (4).

[Math. 3]
$$\nabla f(x) = \left( \frac{df(x)}{da} \quad \frac{df(x)}{dB1} \quad \frac{df(x)}{dT1} \quad \frac{df(x)}{dT2^*} \right) \quad (3)$$

[Math. 4]
$$\nabla^2 f(x) = \begin{pmatrix} \frac{df(x)}{da}\frac{df(x)}{da} & \frac{df(x)}{da}\frac{df(x)}{dB1} & \frac{df(x)}{da}\frac{df(x)}{dT1} & \frac{df(x)}{da}\frac{df(x)}{dT2^*} \\ \frac{df(x)}{dB1}\frac{df(x)}{da} & \frac{df(x)}{dB1}\frac{df(x)}{dB1} & \frac{df(x)}{dB1}\frac{df(x)}{dT1} & \frac{df(x)}{dB1}\frac{df(x)}{dT2^*} \\ \frac{df(x)}{dT1}\frac{df(x)}{da} & \frac{df(x)}{dT1}\frac{df(x)}{dB1} & \frac{df(x)}{dT1}\frac{df(x)}{dT1} & \frac{df(x)}{dT1}\frac{df(x)}{dT2^*} \\ \frac{df(x)}{dT2^*}\frac{df(x)}{da} & \frac{df(x)}{dT2^*}\frac{df(x)}{dB1} & \frac{df(x)}{dT2^*}\frac{df(x)}{dT1} & \frac{df(x)}{dT2^*}\frac{df(x)}{dT2^*} \end{pmatrix} \quad (4)$$

In the calculation of the perturbation of the quantitative value, the standard value of the imaging target set in step S503 is used as the quantitative value.

In order to overestimate the error at the time of deriving a solution due to bad conditions, a threshold value may be set for the number of conditions, and determination of a condition that increases the perturbation when the number is smaller than the threshold value may be set as in the following equation (5).

[Math. 5]
$$(\Delta a \quad \Delta B1 \quad \Delta T1 \quad \Delta T2^*) = 10^{10} \left( \text{if } \det\left( \sum_{i=1}^{N} \nabla^2 f(x_i) \right) \le 10^{-12} \right) \quad (5)$$

Next, the calculated perturbation is normalized and the relative error E is calculated by the following equation (6).

[Math. 6]
$$E = \sum_{j=1}^{M} \left( w_{a,j} \frac{\Delta a_j}{a_j} + w_{B1,j} \frac{\Delta B1_j}{B1_j} + w_{T1,j} \frac{\Delta T1_j}{T1_j} + w_{T2,j} \frac{\Delta T2_j^*}{T2_j^*} \right) \quad (6)$$

Here, M is the number of target tissues (the tissues to be calculated for the quantitative value in the tissues included in the imaging target) and w is a weighting coefficient. Subscript j is an integer of 1 to M and means the quantitative value and the perturbation of each tissue.

In this way, when the quantitative value (reference value) of the target tissue is known in advance, the relative error E can evaluate how much error is included in the quantitative values a, B1, T1, and T2* estimated from the pixel value measured with a certain scan parameter set "xi=(FAi, TRi, TEi, θi)".

The scan parameter set generation unit 430 calculates the relative error for all combination candidates and gives a combination of the scan parameter set "xi=(FAi, TRi, TEi, θi)" having a minimal relative error E as an optimal scan parameter set to the measurement control unit 420 (S5053).

<Steps S504, S506>

FIG. 7(B) illustrates the detail of step S506.

In step S504, when accuracy priority is selected via the selection unit 603 (FIG. 6) and, for example, the value of the relative error E is specified by the user as an index of accuracy, the scan parameter set generation unit 430 extracts a scan parameter set in which the relative error E is smaller than the value specified by the accuracy constraint in the combination (S5061) of the scan parameter set (S5062, S5063) and extracts a scan parameter set having the shortest imaging time among them (S5064). Since the imaging time can be estimated by TR, a scan parameter set that minimizes the total value of TR is extracted here.

<Steps S507, S508>

The measurement control unit 420 acquires N images by executing measurement N times with N types of scan parameters generated in the scan parameter set generation unit 430 using the same pulse sequence. That is, at each measurement, the scan parameters FA, TR, TE, and θ are set to respective values of the scan parameter set generated by the scan parameter set generation unit and the measurement is repeated N times.

<Step S509>

The quantitative value calculation unit 440 estimates the quantitative values a, B1, T1, and T2* by fitting the pixel value Ii of each voxel of the image acquired by the measurement control unit 420 with the scan parameter set "xi=(FAi, TRi, TEi, θi)" using the luminance function f. The fitting solves the least squares problem represented by the following equation (7).

[Math. 7]

$$\text{Min}\left\{\sum_{i=1}^{N}|f(a, B1, T1, T2^*, FA_i, TR_i, \theta_i, TE_i) - I|^2\right\} = \Delta \quad (7)$$

The calculated quantitative value is displayed on the display device 111 by the display control unit 450 if necessary. The display format is the same as the display format for conventional quantitative value imaging. For example, a quantitative value image having a quantitative value as a pixel value may be displayed or the quantitative value may be displayed as a numerical value. Further, it is also possible to calculate other diagnostic quantities using a plurality of quantitative values and to display them.

As described above, in this embodiment, optimal scan parameters for quantitative value estimation under user input conditions are provided. Accordingly, when it is desired to shorten an imaging time while maintaining resolution, for example, the user can easily generate a scan parameter set having a shorter imaging time than the current one by specifying the number of images to be captured or the total TR of the scan parameter sets. Further, when it is desired to focus on the quality of an image, it is possible to easily set a scan parameter set that provides the shortest imaging time while maintaining image quality by specifying the relative error.

Modified Example 1

In the second embodiment, although the pulse sequence for measuring one echo signal in one repetition time TR has been exemplified as an imaging sequence of quantitative value imaging, it is also possible to employ a multi-echo measurement sequence that measures a plurality of echo signals in the TR and acquires a plurality of TE images. As a result, since the number of images acquired in each imaging operation increases, the accuracy of quantitative value estimation can be improved.

Modified Example 2

In the second embodiment, it has been described that parameters having different combinations of at least TR and FA are extracted. However, in this modified example, the phase increment θ of the RF pulse is set to a fixed value and the value is adjusted to an angle different from 117°.

Generally, in a sequence for acquiring an image in which T1 (longitudinal relaxation time) is emphasized, such as an RF-spoiled GRASS sequence, the phase of an RF pulse is changed for each TR in order to eliminate the influence of T2 (lateral relaxation). At this time, it is known that the influence of T2 is effectively eliminated when the phase increment is set to 117°. However, a suitable phase increment for reducing a calculation error of the quantitative value in the quantitative value imaging is not considered. Here, in the modified example, the phase increment is adjusted on the basis of a relationship between the quantitative value calculation error and the phase increment.

Figure 8:
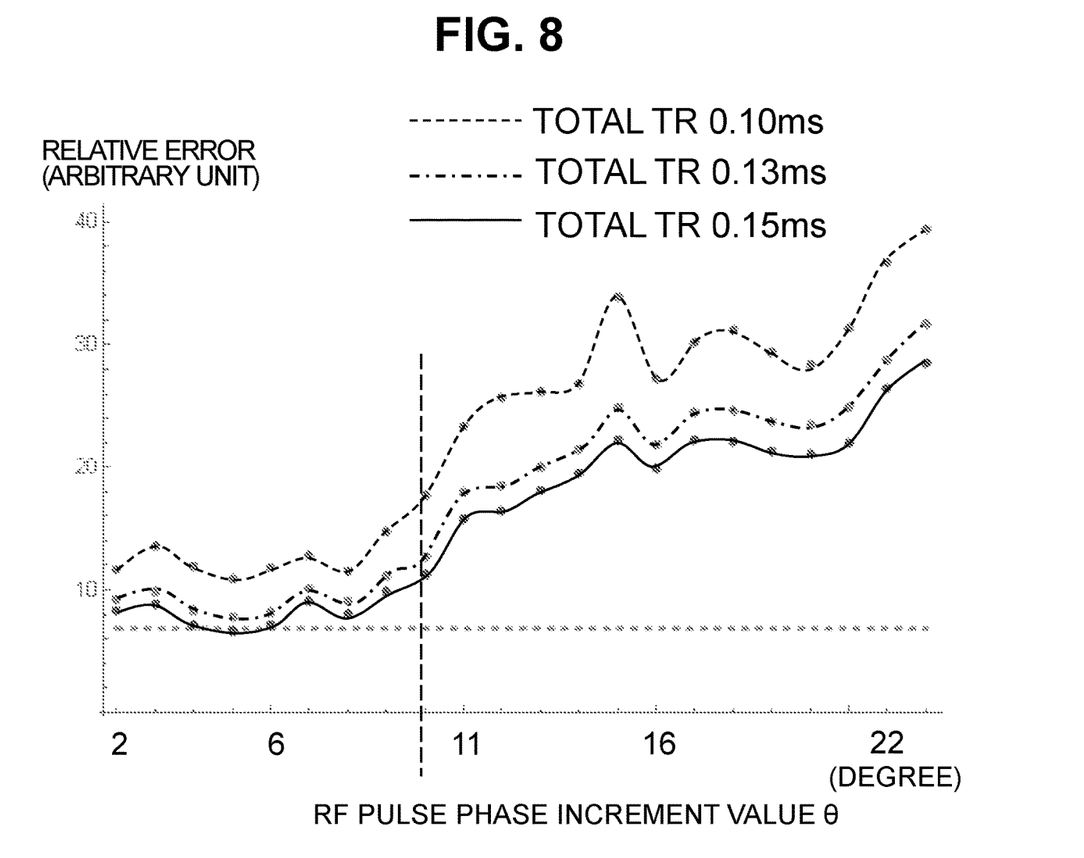
FIG. 8 is a graph showing a relationship between a relative error and a scan parameter.

FIG. 8 shows a diagram in which the value of the relative error E when the value of θ which is a fixed value is changed is plotted. The relative error E is a value calculated by applying various values of θ to the above-described equations (2) and (6) and a case in which different total values of TR are plotted in the graph. As understood from the drawing, there is a tendency that the relative error E increases in accordance with an increase in the phase increment when the phase increment value θ exceeds 10° in any TR.

Here, in this modified example, the scan parameter set setting unit 430 generates a scan parameter set by combining other scan parameter value candidates after setting the phase increment to a fixed value of 10° or less (0° or more and 10° or less). This is the same as the second embodiment in that the combination of the scan parameter set in which the relative error E is minimal is determined by calculating the relative error E under the constraint for the error accuracy or the constraint for the time in the plurality of generated scan parameter sets.

According to this modified example, it is possible to increase the error accuracy by adjusting the phase increment value.

Further, the scan parameter set may be calculated by changing θ in each scan parameter set without fixing the value of the phase increment value θ instead of setting the phase increment value θ to a fixed value of 10° or less. Accordingly, there is an advantage that the quantitative value accuracy can be further improved.

Modified Example 3

In the second embodiment, the scan parameter set generation unit 430 executes a calculation on the basis of the specification of the user, but an optimal scan parameter set may be calculated in advance under a plurality of conditions, listed, and stored in the storage device 112. In that case, the scan parameter set generation unit 430 extracts the scan parameter set matching the specified condition by referring to the information stored in the storage device 112 and presents the extracted one as an optimal parameter set. Accordingly, the processing time from setting to receiving the presentation of the optimal parameters can be greatly reduced and the convenience is improved.

Third Embodiment

In the above-described embodiments, a case in which a function of generating the scan parameter set of the invention is executed by the computer in the MRI device has been described, but the function of generating the scan parameter set can be executed by another computer different from the MRI device. The another computer may be an independent CPU or may be built on a cloud and is included in the invention as a scan parameter set generation device.

Figure 9:
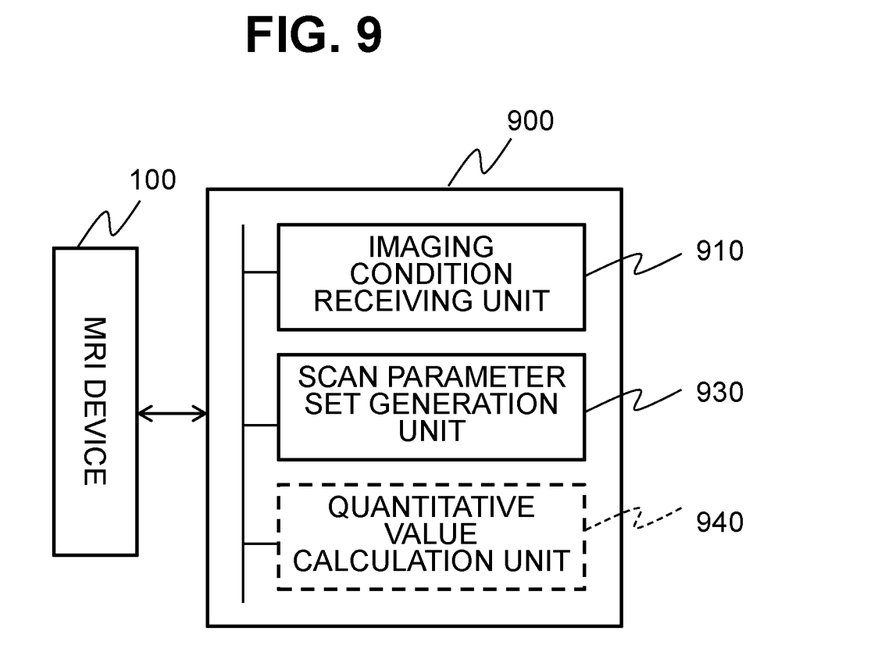
FIG. 9 is a functional block diagram of a scan parameter set generation device of a third embodiment.

In this case, a scan parameter set generation device 900 includes, as illustrated in FIG. 9, a receiving unit 910 which receives an imaging condition received by the imaging condition receiving unit 10 of the MRI device 100 and a scan parameter set generation unit 930. When the scan parameter set generation device 900 is a device which can be connected to the MRI device 100 via a network, the receiving unit 910 receives an imaging condition received by the imaging condition receiving unit 10 of the MRI device capturing a predetermined imaging target via a network, a communication unit, or a portable medium or the like. The scan parameter set generation unit 930 may include an input device used to input an imaging condition by the user.

A procedure of generating the scan parameter set by the scan parameter set generation unit 930 is the same as the procedure (FIG. 5) executed by the scan parameter set generation unit 430 in the MRI device and is executed according to, for example, a program describing the following procedure.

The procedure includes a step (S501) of receiving the imaging target, a step (S502) of receiving constraint conditions on the imaging time or the estimation accuracy of the quantitative value, a step (S503) of setting the quantitative value information (the standard value of the quantitative value) in the imaging target on the basis of the received imaging target, a step (S504) of determining whether the specified constraint condition is for time or accuracy, a step (S505) of calculating at least three or more scan parameter sets in which the combination of at least the repetition time and the flip angle is different and the quantitative value estimation error is minimal while satisfying the specified time constraint according to the error propagation method using the standard value of the quantitative value when it is determined that the time constraint is received, and a step (S506) of calculating at least three or more scan parameter sets in which the combination of at least the repetition time and the flip angle is different and the imaging time is minimal while satisfying the specified accuracy constraint according to the error propagation method when it is determined that the accuracy constraint is received.

For example, the process of step S505 can include, as illustrated in FIG. 7(A), step S5051 of generating combination candidates of a plurality of scan parameter set by using an index relating to a time, that is, under a constraint relating to a time. Alternatively, the combination candidates can be prepared as database in advance. In that case, in step S501, for example, a combination of scan parameter sets to be optimized may be selected from the candidates in the database. Further, the process of step S505 can include a step (S5052) of calculating a relative error using a standard value of a quantitative value in the combination candidate generated in S5051 and step (S5053) of determining a combination of a scan parameter set having a minimal error by the error propagation method.

The process of step S506 can include, as illustrated in FIG. 7(B), step S5061 of generating a combination candidate, step S5062 of calculating a relative error, step S5063 of selecting a combination in which a relative error is equal to or smaller than a specified error accuracy, and step S5064 of selecting a combination having a shortest imaging time from the combination selected in step S5063.

According to this embodiment, since the scan parameter set is generated by the computer independent from the MRI device, it is possible to reduce the load of the calculation unit (CPU) of the MRI device.

Furthermore, the parameter set generation device 900 of this embodiment may include a quantitative value calculation unit 940 (indicated by a dotted line) in addition to the scan parameter set generation unit 930. In this case, the quantitative value calculation unit 940 acquires a plurality of images captured by the MRI device 100 using the scan parameter set generated by the scan parameter set generation device 900 and calculates the quantitative value. The calculated quantitative value is returned to the MRI device and is displayed in the MRI device 100 together with other images (for example, images used for calculating the quantitative value). The form of display is arbitrary.

REFERENCE SIGNS LIST

10 Imaging condition receiving unit
20 Measurement unit
30 Scan parameter set generation unit
40 Quantitative value calculation unit
100 MRI device
101 Magnet
102 Gradient magnetic field coil
103 Subject (living body)
104 Sequencer
105 Gradient magnetic field power supply
106 High-frequency magnetic field generator
107 RF coil
108 RF probe
109 Receiver
110 Computer
111 Display device
112 Storage device
113 SIMM coil
114 SIMM power supply
115 Bed (table)
116 Input device
410 Imaging condition receiving unit
411 Target receiving unit
412 Constraint condition receiving unit
420 Measurement control unit
430 Scan parameter set generation unit
440 Quantitative value calculation unit
450 Display control unit
900 Scan parameter set generation device
910 Receiving unit
930 Scan parameter set generation unit
940 Quantitative value calculation unit

The invention claimed is:

1. A magnetic resonance imaging device comprising:
a measurement unit which captures N images of the same imaging target by executing an imaging sequence using at least a repetition time TR and a flip angle FA as a scan parameter N times (N is 3 or more) by changing a combination of the values of the repetition time TR and the flip angle FA;
a quantitative value calculation unit which calculates one type or more of quantitative values on the basis of N images captured by the measurement unit;
a scan parameter set generation unit which generates N types of combinations of the repetition time TR and the flip angle FA and sets the combination as the repetition time TR and the flip angle FA when the measurement unit executes the imaging sequence N times; and
a target receiving unit which receives information specifying the imaging target from a user,
wherein the scan parameter set generation unit selects a standard value of a quantitative value of the imaging target received by the target receiving unit from standard values of one type or more of quantitative values obtained in advance for the plurality of imaging targets and generates N types of combinations of the values of the repetition time TR and the flip angle FA in which an imaging time of the imaging sequence is equal to or smaller than a predetermined value or an error of the quantitative value calculated by the quantitative value calculation unit is equal to or smaller than a predetermined value by using the standard value of the quantitative value.

2. The magnetic resonance imaging device according to claim 1,
wherein the scan parameter set generation unit generates N types of combinations of values of the repetition time TR and the flip angle FA by calculating an error estimation value of the quantitative value using the standard value of the quantitative value for a plurality of candidates of N types of predetermined combinations of the values of the repetition time TR and the flip angle FA and selecting a candidate in which an imaging time of the imaging sequence is equal to or smaller than a predetermined value or the error estimation value of the quantitative value calculated by the quantitative value calculation unit is equal to or smaller than a predetermined value.

3. The magnetic resonance imaging device according to claim 2,
wherein the scan parameter set generation unit generates N types of combinations of the repetition time TR and the flip angle FA by selecting a plurality of candidates in which an imaging time of the imaging sequence is equal to or smaller than a predetermined value as the plurality of candidates and selecting a candidate in which an error estimation value of the quantitative value calculated by the quantitative value calculation unit is minimal from the plurality of selected candidates.

4. The magnetic resonance imaging device according to claim 2,
wherein the scan parameter set generation unit generates N types of combinations of the repetition time TR and the flip angle FA by calculating an error estimation value of the quantitative value using the standard value of the quantitative value for the plurality of candidates and selecting a candidate in which an imaging time of the imaging sequence is shortest from a plurality of candidates in which the calculated error estimation value is equal to or smaller than a predetermined value.

5. The magnetic resonance imaging device according to claim 1, further comprising:
a constraint condition receiving unit which receives a user's selection for any one of the "imaging time" and the "error of the quantitative value",
wherein the scan parameter set generation unit generates N types of combinations of the values of the repetition time TR and the flip angle FA in which an imaging time of the imaging sequence is equal to or smaller than a predetermined value when the selection received by the constraint condition receiving unit is the "imaging time", and generates N types of combinations of the values of the repetition time TR and the flip angle FA in which an error of the quantitative value calculated by the quantitative value calculation unit is equal to or smaller than a predetermined value when the selection received by the constraint condition receiving unit is the "error of the quantitative value".

6. The magnetic resonance imaging device according to claim 5,
wherein the constraint condition receiving unit further receives a user's selection for any one of a value of the imaging time and a value of the error of the quantitative value.

7. The magnetic resonance imaging device according to claim 1,
wherein the one type or more of quantitative values include one type or more of physical property values of the imaging target and the one type or more of physical property values include any one of a proton density and a longitudinal relaxation time T1 and a lateral relaxation time T2 or an apparent lateral relaxation time T2*.

8. The magnetic resonance imaging device according to claim 1,
wherein the scan parameter set generation unit sets an RF phase increment value to a fixed value of a predetermined range in a generated scan parameter set having a different combination of the repetition time and the flip angle.

9. The magnetic resonance imaging device according to claim 8,
wherein the RF phase increment value is adjusted to a value satisfying 0° or less and 10° or more.

10. A calculation device for generation of a scan parameter set comprising:
a target receiving unit which receives information specifying a target captured by using an imaging sequence for obtaining a quantitative value image by a magnetic resonance imaging device from a user; and
a scan parameter set generation unit which generates N types of combinations of values of a repetition time TR and a flip angle FA of the imaging sequence,
wherein the scan parameter set generation unit selects a standard value of a quantitative value of an imaging target received by the target receiving unit from standard values of one type or more of quantitative values obtained in advance for a plurality of imaging targets, calculates an error of the quantitative value obtained by the imaging operation using the standard value of the quantitative value, and generates N types of combinations of values of the repetition time TR and the flip angle FA in which an imaging time of the imaging sequence is equal to or smaller than a predetermined value or the error of the quantitative value is equal to or smaller than a predetermined value.

11. The calculation device for generation of the scan parameter set according to claim 10, further comprising:
a quantitative value calculation unit which acquires N images captured by the magnetic resonance imaging device by using N types of combinations of the values of the repetition time TR and the flip angle FA generated by the scan parameter set generation unit and generates a quantitative value image by using the N images and the values of the repetition time TR and the flip angle FA.

12. A scan parameter set generation program for causing a computer to execute steps of:
receiving information specifying an imaging target;
selecting a standard value of a quantitative value of the imaging target received in the receiving step from standard values of one type or more of quantitative values obtained in advance for a plurality of imaging targets;
calculating an error estimation value of the quantitative value obtained from an image captured by using a combination of each scan parameter set in a combination of a plurality of scan parameter sets using the selected standard value of the quantitative value; and
determining N (N is an integer of 3 or more) types of combinations of optimal scan parameter sets by using an index relating to an imaging time and the error estimation value of the quantitative value as constraints.

13. A magnetic resonance imaging device comprising:
a target receiving unit which receives information specifying an imaging target from a user;
a measurement unit which acquires a plurality of images of the imaging target by executing measurement a plurality of times;
a quantitative value calculation unit which calculates a quantitative value of the imaging target by using the plurality of images acquired by the measurement unit; and
a scan parameter set generation unit which generates a scan parameter set used for the plurality of measurements, wherein the scan parameter set generation unit estimates an error of the quantitative value when a value of a scan parameter is changed by using information specifying the imaging target received by the target receiving unit and determines a combination of the scan parameters by using an index relating to an imaging time and an error estimation value.

* * * * *